United States Patent [19]

Wilson

[11] Patent Number: 4,854,866

[45] Date of Patent: Aug. 8, 1989

[54] METHOD AND APPARATUS FOR USE IN CONSTRUCTING AN ORTHODONTIC APPLIANCE

[76] Inventor: William L. Wilson, 15 Dix St., Winchester, Mass. 01890

[21] Appl. No.: 140,038

[22] Filed: Dec. 31, 1987

[51] Int. Cl.$^4$ ............................................... A61K 7/00
[52] U.S. Cl. ...................................................... 433/24
[58] Field of Search .............................. 433/24, 37, 44

[56] References Cited

U.S. PATENT DOCUMENTS 3,949,478  4/1976  Schimnammer ........................ 433/24

Primary Examiner—Robert Peshock
Attorney, Agent, or Firm—Sheridan, Ross & McIntosh

[57] ABSTRACT

Method and apparatus are provided for fabricating a precisely dimensioned orthodontic appliance. The apparatus includes a lingual tube/molar band assembly having a molar band attached to a patient's teeth and one or more lingual tubes. The apparatus also includes a transfer insert for use as a marking device and transfer lingual tubes, corresponding to the lingual tubes of the lingual tube/molar band assembly. In practicing the method, the transfer insert is seated in the lingual tubes of the lingual tube/molar band assembly. A negative impression is then taken with the transfer insert being absorbed into the impression material. The location of the lingual tubes are marked in the negative impression using the transfer insert. The transfer lingual tubes are then joined to the transfer insert. Stone is then poured into the negative impression to create the positive model of the patient's teeth. Upon separation of the negative impression from the stone cast, the transfer lingual tubes adhere to the positive model while the transfer insert remains with the negative impression. Since the location of the transfer lingual tubes in the stone model precisely matches the position of the lingual tubes in the patient's mouth, a precisely dimensioned orthodontic appliance can then be fabricated using the positive model and the transfer lingual tubes.

22 Claims, 4 Drawing Sheets

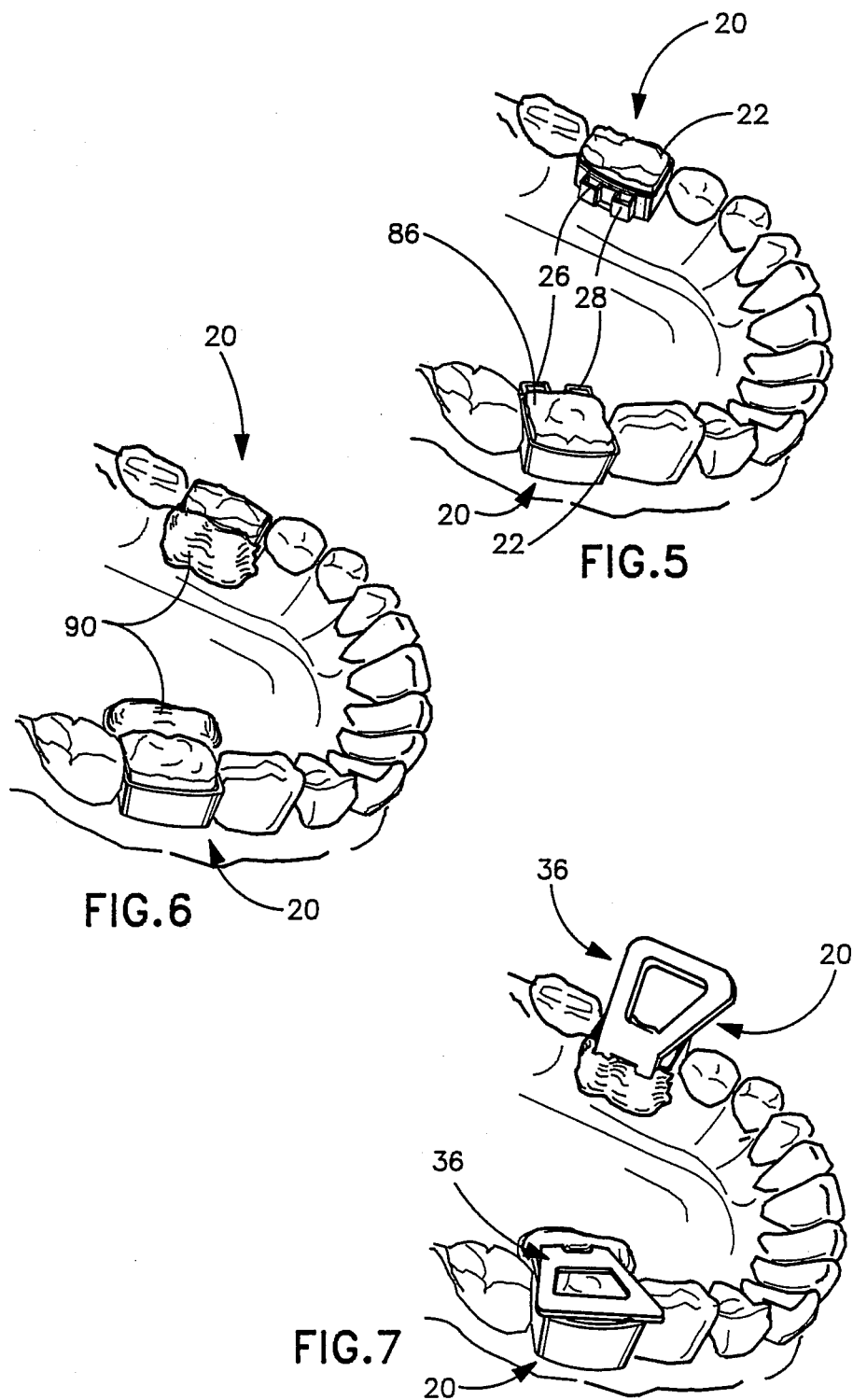

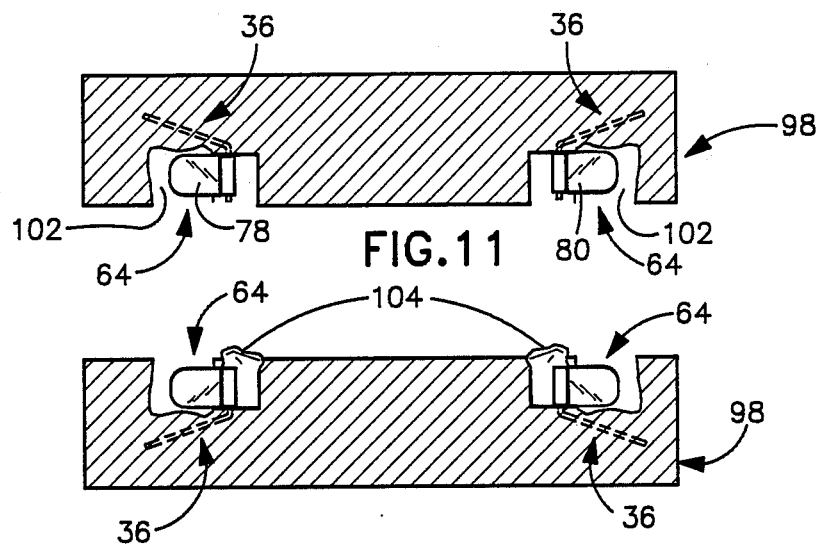
FIG.11
FIG.12
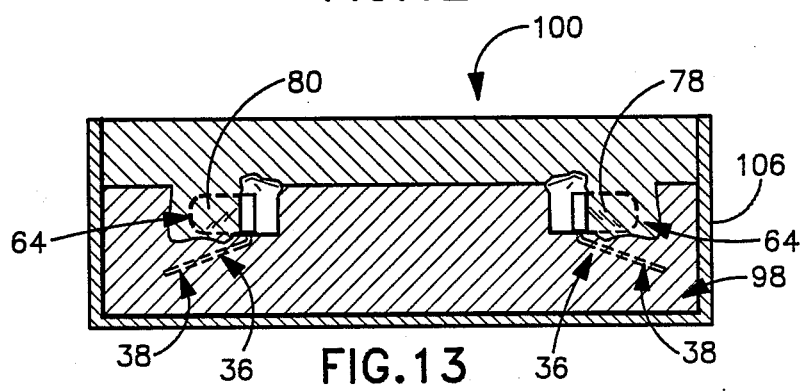
FIG.13
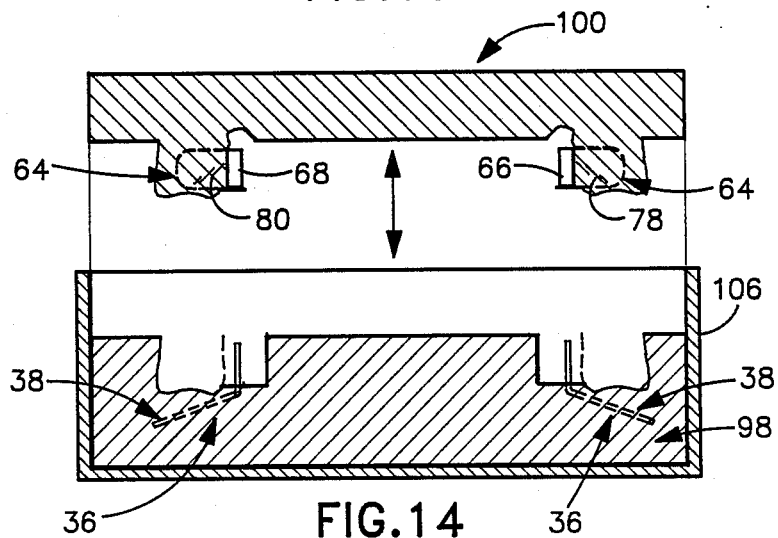
FIG.14

METHOD AND APPARATUS FOR USE IN CONSTRUCTING AN ORTHODONTIC APPLIANCE

FIELD OF THE INVENTION

This invention relates to a method, and the associated apparatus, for fabricating a precisely dimensioned orthodontic appliance using a marking device and a stone casting, which models the patient's dental structure.

BACKGROUND OF THE INVENTION

The correction of certain malocclusions is traditionally accomplished by means of wire structures anchored to the patient's teeth. The wire structures are known as arches or arch wires and the anchoring assembly generally has one or more lingual tubes attached to a molar band. Generally, two such lingual tube/molar band assemblies are attached to the patient's teeth to anchor the ends of an arch wire. Each teeth to become properly aligned. Integral to the arch wire are posts which are seated into the lingual tubes of the anchoring assembly thereby anchoring the arch wire in place.

Fabrication of the customized arch wire is accomplished by first constructing a stone model of the patient's dental structure using a negative impression of the dental structure as is well known in the art. Based on the model an arch wire or orthodontic appliance can be constructed to correct the malocclusions. While the model is adequate for defining certain characteristics of the orthodontic appliance it does not accurately represent the location of the lingual tubes. Consequently, certain characteristics of the orthodontic appliance, which depend upon the location of the lingual tubes, can only be estimated by the orthodontist or dental practitioner. This deficiency results in orthodontic appliances being fabricated which may require significant manipulation by the orthodontist or dental practitioner in order to fit the appliance to the patient's teeth. However, such manipulation may render the orthodontic appliance unsuitable and thereby require the fabrication of a new appliance.

For example, arch wires fabricated according to traditional techniques and which are anchored by horizontal lingual tubes, are typically in error by about twenty thousandths of an inch at each end. That is, the horizontal lingual tube is typically offset from its desired position relative to a patient's tooth by this amount. While this may appear to be an insignificant amount, the adjustments that would be required to make such an arch both fit and perform properly would generally render the arch useless for its intended purpose. Improved results can be obtained by using a single vertical lingual tube, but adjustments are still required. Consequently, there is a need for a method which produces highly precise orthodontic appliances without subsequent adjustments thereof.

The present invention is intended to eliminate the necessity of gross manipulations of orthodontic appliances constructed using stone models by precisely locating lingual tubes on the stone model. Consequently, only the most minor adjustments, if any, need to be made when fitting the appliance to the patient's teeth and the need to refabricate the appliance is thereby minimized.

SUMMARY OF THE INVENTION

A primary objective of the present invention is to provide a method, together with associated parts, for creating a precisely dimensioned orthodontic appliance using a stone casting, which represents the patient's dental structure. The component parts of the invention include a twin lingual tubes/molar band assembly, a transfer insert, a soft colloid impression material, one or more transfer lingual tubes, and casting material for the stone model.

The first step in creating a precisely dimensioned orthodontic appliance for a particular patient is by adapting the twin lingual tubes/molar band assembly to the patient's teeth. The lingual tubes are the anchoring pieces to which the orthodontic appliance is connected when positioned adjacent to the patient's teeth. The lingual tubes are prewelded to the molar band. Because the lingual tubes provide the anchor for the orthodontic appliance or arch wire, they also define certain dimensions of the orthodontic appliance. Consequently, it is necessary to preserve each location of a lingual tube so that it can be transferred to the stone casting from which the orthodontic appliance is to be made.

The next step in the creation of a precisely dimensioned orthodontic appliance is, preferably, to coat each of the lingual tubes with wax to promote the retention of the transfer insert which is later seated in the twin lingual tubes.

Third, the transfer insert is seated in the lingual tubes. The transfer insert precisely marks the location of the lingual tubes in the negative impression that is taken of the patient's dental structure. Basically, the transfer insert includes two posts attached to a trapezoidal-like structure. Each of the two posts fits into one of the twin lingual tubes and thereby defines the location of each of the lingual tubes in the negative impression. The design of the trapezoidal-like structure serves both to promote the absorption of the transfer insert into a soft colloid impression material as well as secure the transfer insert therein.

Fourth, a negative impression of the patient's dental structure is taken in a manner well known in the art. The negative impression provides the mold for the positive stone casting of the patient's dental structure. The trapezoidal-like structure of the transfer insert is absorbed and retained in the soft colloid material used to take the negative impression. Consequently, when the soft colloid impression material is removed from the patient's mouth the transfer insert comes with it. The location of the lingual tubes is now precisely marked in the negative impression by means of the transfer insert.

Fifth, approximately, 3 millimeters (mm) of the soft colloid impression material is, preferably, removed from the lingual side of the transfer insert posts located in the negative impression. This procedure ensures that there is sufficient space to seat the transfer lingual tubes, which substantially model the lingual tubes of the twin lingual tubes/molar band assembly located in the patient's mouth, on the transfer insert posts.

Sixth, the transfer lingual tubes, which substantially model the lingual tubes located in the patient's teeth, are seated on the posts of the transfer insert protruding from the negative impression. The transfer lingual tubes are now positioned precisely as the lingual tubes located in the patient's mouth. The transfer lingual tubes include one or more lingual tubes, corresponding to those in the patient's mouth, and which are prewelded to two integrally formed retention tabs. The retention tabs are used to attach the transfer lingual tubes to the positive stone casting that is created from the negative impression.

Seventh, in anticipation of making the positive stone casting the transfer lingual tubes and any of the 3 mm space still remaining is preferably filled with wax. This procedure prevents the casting material from cementing the transfer insert and transfer lingual tubes together Consequently, the separation of the positive casting having the transfer lingual tubes from the negative mold having the transfer insert is facilitated.

Finally, a positive cast which accurately models the patient's dental structure and, in addition, has lingual tubes located at precisely the same locations as the ones in the patient's mouth is produced. The positive cast is created by pouring a casting material into the negative impression. As previously discussed, the negative impression contains the transfer lingual tubes which have been positioned using the transfer insert which, in turn, was positioned using the patient's lingual tubes. The casting material cements the retention tabs of the transfer lingual tubes in place. However, the casting material does not bond the transfer insert and the transfer lingual tubes together because of the wax previously mentioned. As a result, once the casting material cures and the positive and negative casts or impressions are separated, the positive model of the patient's dental structure contains the transfer lingual tubes positioned precisely as the lingual tubes in the patient's mouth.

An orthodontic appliance can now be constructed based on the stone casting. Since the stone casting models both the patient's dental structure and the location of the lingual tubes a precise orthodontic appliance can be constructed to remedy the patient's malocclusion. Due to the precision of the resulting orthodontic appliance several advantages are realized. Among the advantages is the minimization of gross adjustments which could render the orthodontic appliance useless. Concomitantly, the amount of time a patient must spend in the dentist's chair, together with the associated discomfort, is reduced. Furthermore, the resulting model with the attached lingual tubes provides the practitioner with a permanent record that can possibly be used with other appliances during treatment of the patient's malocclusion.

BRIEF DESCRIPTION OF THE DRAWINGS

FIG. 5 is a perspective view of the lower teeth with a twin lingual tubes/molar band assembly attached to each molar;

FIG. 6 is a perspective vice of the lower teeth with wax covering the lingual tubes;

FIG. 7 is a perspective view of the lower teeth with the transfer insert attached to the lingual tubes;

FIG. 11 is a cross sectional view of the negative impression with the transfer lingual tubes seated on the transfer inserts;

FIG. 12 is a cross sectional view of the negative impression inverted for placement in the casting tray and with wax located in both the 3 mm gap and the open end of the transfer lingual tubes;

FIG. 13 is a cross sectional view of the negative impression and the corresponding positive casting;

FIG. 14 is a cross sectional view of the negative impression with the attached transfer insert and the positive casting with the attached transfer lingual tubes.

DETAILED DESCRIPTION OF THE PREFERRED EMBODIMENT

Figure 1:
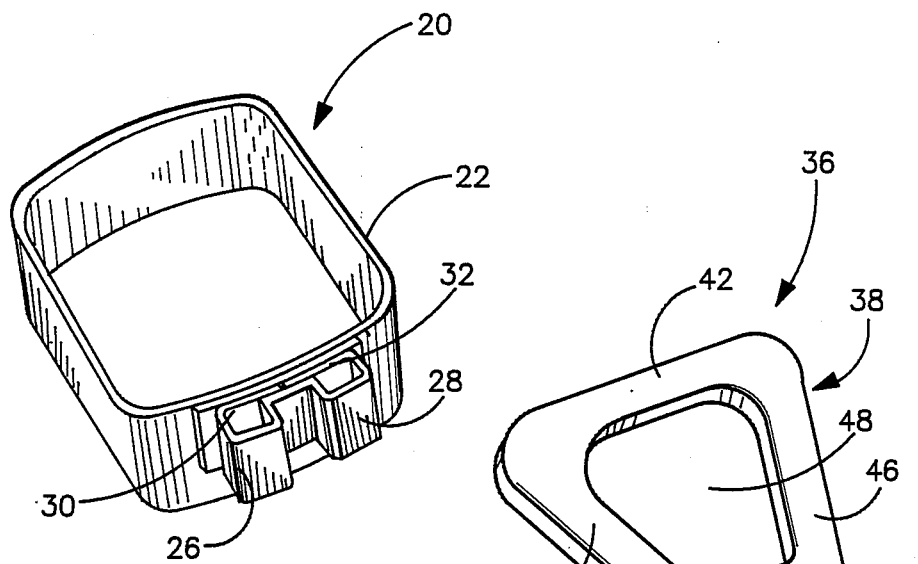
FIG. 1 is a perspective view of the twin lingual tubes/molar band assembly.

In accordance with the present invention, method and apparatus are provided for producing a precisely dimensioned orthodontic appliance, such as an arch wire. With reference to FIGS. 1-5, the apparatus includes, preferably, a twin lingual tubes/molar band assembly 20 adapted to a molar of the patient's teeth. While the described apparatus and method utilize a twin configuration in order to achieve greater precision, a less precise single configuration could also be used. The twin lingual tubes/molar band assembly 20 includes a molar band 22 to which lingual tubes are attached. In the illustrated embodiment, the lingual tubes include two vertically disposed parallel tubes 26, 28 which have open ends 30, 32, respectively. As can be seen in FIG. 5, two twin lingual tubes/molar band assemblies 20 are illustrated with each molar band 22 thereof surrounding a molar of the patient's bottom teeth.

Figure 2:
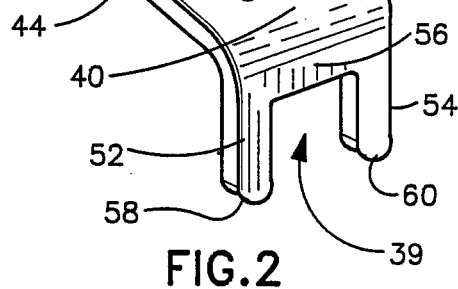
FIG. 2 is a perspective view of the transfer insert.
Figure 3:
FIG. 3 is a side view of the transfer insert.

With particular reference to FIGS. 2-3, the apparatus also includes a transfer insert 36, which is joined to the twin lingual tubes/molar band assembly 20 in practicing the method of the present invention. The transfer insert 36 includes a retention member 38 integrally joined to a marking member 39. The retention member 38 includes two parallel cross members 40, 42 which are joined together by diverging side members 44, 46 to define a trapezoidal construction having an opening 48 that promotes absorption of the retention member 38 into a soft colloid impression material. The trapezoidal shape of the retention member 38 serves to create a wedge which prevents the transfer insert 36 from coming out of a soft colloid impression material while practicing the inventive method. Likewise, the retention member 38 is angularly disposed relative to the marking member 39 to prevent the transfer insert 36 from coming out of a soft colloid impression material. With continued reference to FIGS. 2-3, the marking member 39 includes two vertically disposed parallel posts 52, 54 which are joined at one end by a post cross member 56. The other ends of the posts 52, 54 are free ends 58, 60. Each of the free ends 58, 60 is of a size to be received in one of the open ends 30, 32 respectively, of the twin lingual tubes/molar band assembly 20.

Figure 4:
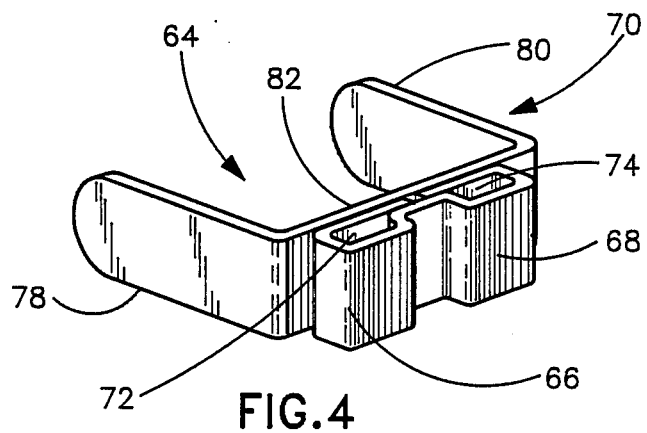
FIG. 4 is a perspective view of the transfer lingual tubes/holding device assembly.

With particular reference to FIG. 4, the apparatus further includes a transfer lingual tubes/holding device assembly 64 defined by a pair of transfer lingual tubes 66, 68 attached to a holding device 70. The transfer lingual tubes 66, 68 are two vertically disposed parallel tubes and each has an open end 72, 74, respectively. The open ends 72, 74 are of a size to matingly engage or receive the posts 52, 54, respectively, of the transfer insert 36. The transfer lingual tubes 66, 68 match or correspond to the lingual tubes 26, 28 fastened to the patient's teeth. The holding device 70 includes a U-shaped strip of metal. The transfer lingual tubes 66, 68 are attached to the middle portion 82 of the holding device 70. Retention tabs 78, 80 make up the remainder of the holding device 70. The tabs 78, 80 anchor the transfer lingual tubes/holding device assembly 64 to a stone model of the patient's teeth, while using the inventive method, which is next to be described.

With further reference to FIG. 5, the initial step in the fabrication of a precision orthodontic appliance is to attach the twin lingual tubes/molar band assemblies 20 to anchoring molars 86. Attachment is accomplished by cementing the molar band 22 to the anchoring molar 86. The lingual tubes 26, 28 receive the posts of the resulting orthodontic appliance and thereby anchor the appliance in place in the patient's mouth. Since the lingual tubes 26, 28 receive the posts of the resulting orthodontic appliance they also, necessarily, define certain dimensions of the appliance. Consequently, the location of each of the lingual tubes 26, 28 must be preserved so that the position of each lingual tube 26, 28 is duplicated in the stone model from which the appliance is ultimately fabricated. The lingual tubes 26, 28 also receive the posts 52, 54, respectively, of the transfer insert 36, as will be described more fully later, thereby preserving each location.

With reference to FIG. 6, the second step in the fabrication of the orthodontic appliance is to preferably cover the open ends 30, 32 of the lingual tubes 26, 28 with wax 90. The wax 90 promotes the retention of transfer insert 36 in lingual tubes 26, 28.

With reference to FIG. 7, the third step in the fabrication of the appliance is to seat the transfer insert 36 in the lingual tubes 26, 28 of the twin lingual tubes/molar band assembly 20. The transfer insert 36 is seated by placing the free ends 58, 60 of the transfer insert posts 52, 54 in the open ends 30, 32, respectively, of the lingual tubes 26, 28. This results in the retention member 38 of the transfer insert 36 being disposed over the anchoring molar 86. Alternatively, it may be desirable to place the free ends 58, 60 in the open ends 32, 30, respectively, which results in the retention member 38 being oppositely disposed. In either case, the transfer insert 36 ultimately serves to preserve the location of the lingual tubes 26, 28 in, in the illustrated case, a negative impression 98 of the patient's bottom teeth. The location of the lingual tubes 26, 28 can then be transferred from the negative impression 98 to form a positive model or cast of the patient's dental structure, as described more fully later.

Figure 8:
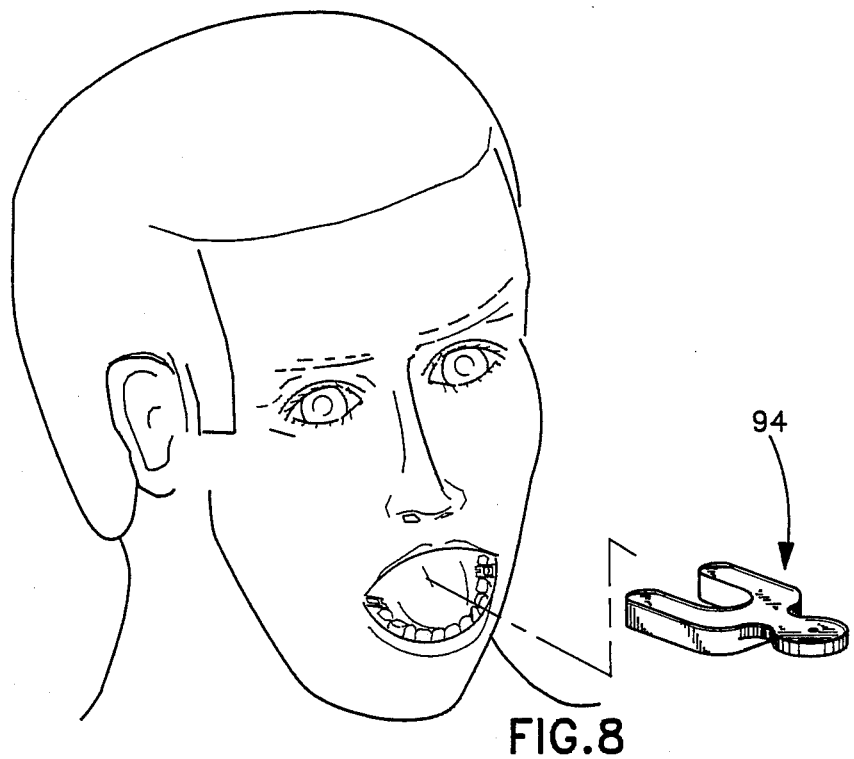
FIG. 8 illustrates the taking of a negative impression by insertion of a soft colloid impression material into the patient's mouth.
Figure 9:
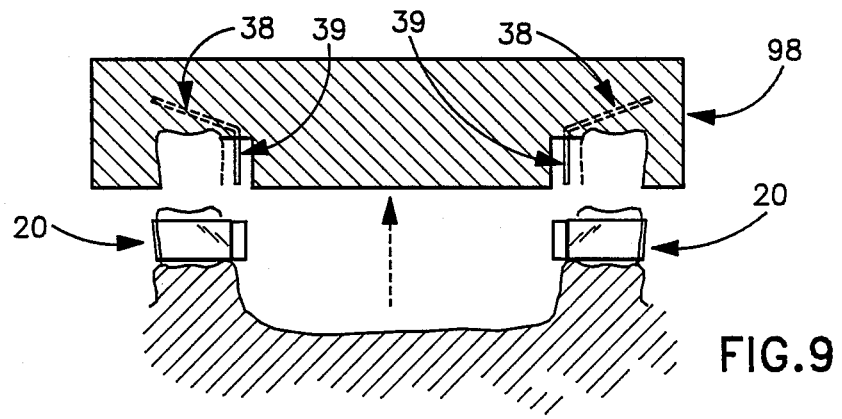
FIG. 9 is a cross sectional view of the lower molars with their attached lingual tubes and the negative impression containing the transfer insert.

With reference now to FIGS. 8 and 9, the fourth step in the fabrication of the orthodontic appliance is to obtain the negative impression 98 of the patient's teeth. The negative impression 98 is achieved by inserting the soft colloid impression material 94 into the patient's mouth. Pressure is then applied to the soft colloid impression material 94 to force it to flow around the patient's teeth and thereby produce the negative impression 98.

As previously mentioned, the posts 52, 54 of the transfer insert 36 mark the location of the lingual tubes 26, 28 in the negative impression 98. Consequently, the transfer insert 36 must be transferred to the soft colloid impression material 94. As pressure is applied to soft colloid impression material 94 it flows around and absorbs the retention member 38 of the transfer insert 36. The opening 48 promotes this absorption process as it permits the soft colloid impression material 94 to easily flow around and adhere to the integral pieces of the retention member 38. Conversely, the retention member 38 was incorporated into the transfer insert 36 to insure that the transfer insert 36 remains in the soft colloid impression material 94 upon its removal from the patient's mouth. Both the trapezoidal configuration of retention member 38 and the angular disposition of retention member 38 relative to marking member 39 serve to prevent removal of the transfer insert 36 from the soft colloid impression material 94. Retention of the transfer insert 36 in the soft colloid impression material 94 is also necessary for subsequent steps in the method.

Figure 10:
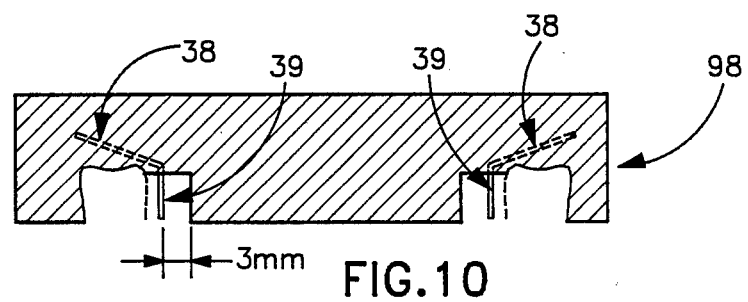
FIG. 10 is a cross sectional view of the negative impression with about 3 mm of the impression material removed from the lingual side of the transfer insert.

With reference to FIG. 10, the next step in the fabrication of the orthodontic appliance is to preferably scrape approximately 3 mm of the soft colloid impression material 94 from the lingual side of the posts 52, 54 of the transfer insert 36 located in negative impression 98. This step is intended to insure that there is adequate seating clearance for the transfer lingual tubes/holding device assembly 64.

With reference to FIG. 11-13, a subsequent step in the fabrication of the appliance is to seat the transfer lingual tubes/holding device assembly 64 on the posts 52, 54 of the transfer insert 36. The transfer lingual tubes 66, 68 are substantially the same as the lingual tubes 26, 28 previously joined to the patient's teeth. The open ends 72, 74 of the transfer lingual tubes 66, 68 receive the posts 52, 54, respectively, of the transfer insert 36, which are protruding from the negative impression 98. The retention tabs 78, 80 extend into a cavity 102 of the negative impression 98 which is to be substantially filled with casting material to form the positive cast 100.

With reference to FIG. 12, an additional, preferred step in the fabrication of the orthodontic appliance is to apply wax 104 to whatever remains of the 3 mm space and also to apply the wax to the open ends 72, 74 of the transfer lingual tubes 66, 68. This prevents the transfer lingual tubes/holding device assembly 64 from adhering to the transfer insert 36 when the stone is poured to make the positive cast.

With reference to FIGS. 13 and 14, the final step in fabrication of the precision orthodontic appliance is to make the positive cast 100 of the patient's dental structure. The negative impression 98 is placed in casting tray 106. Casting material is then poured into negative impression 98 to create the positive casting 100. Once the stone has cured, the positive casting 100 and the negative impression 98 are separated. The transfer insert 36 remains in the negative impression 98 due to the retention member 38. Likewise, the casting material of the positive casting 100 adheres to the retention tabs 78, 80 thereby causing a transfer of the transfer lingual tubes/holding device assembly 64 from the negative impression 98 to the positive casting 100. That is, the transfer lingual tubes 66, 68 become positioned on the positive casting 100 at an area, or casted tooth portion, corresponding to the area, or portion, of the patient's teeth having the lingual tubes 26, 28. Further, the retention tabs 78, 80 act to hold the transfer lingual tubes 66, 68 at the desired location relative to the teeth of the positive casting 100. Thus, the positive casting 100 can be used to fabricate a precise orthodontic appliance to correct one or more malocclusions present in a patient's teeth.

Based on the foregoing description, a number of advantages of the present invention are immediately discerned. Among the advantages a method and apparatus are provided for positioning lingual tubes with great accuracy relative to the stone mold of a patient's teeth. As a result, a very precise orthodontic appliance, such as an arch wire, can be fabricated using the stone model. This enables the orthodontist to reduce the time that the patient must spend being fitted with the arch wire and the necessary discomfort that accompanies the fitting process. Importantly also, relatively gross changes or manipulations of the arch wire while it is being fitted to the patient's teeth are reduced because of the high degree of accuracy obtained using the positive casting of the present invention. Concomitantly, there is less likelihood that the arch wire will be rendered unsuitable or useless because of later effected changes during the time that the patient is being fitted with the arch wire.

While the apparatus and method herein described constitutes the preferred embodiment of the invention, it is to be understood that the invention is not limited to this exact apparatus and method, and that changes can be made without departing from the scope of the invention, which is defined in the appended claims. For example, the apparatus and associated method could also be practiced on the patient's upper teeth.

What is claimed is:

1. A method for constructing a precise orthodontic appliance for a patient's teeth, comprising:
   occupying a predetermined point in spaced relative to a patient's teeth using marking means, wherein said predetermined point is interior a space defined by an appliance attached to the patient's teeth;
   positioning anchoring means in a positive cast using said marking means wherein said anchoring means defines but does not occupy said point in space; and
   fabricating a precise orthodontic appliance for the patient's teeth using said anchoring means and said positive cast.

2. A method, as claimed in claim 1, wherein:
   said step of occupying a predetermined location includes attaching band means to a patient's teeth and attaching said marking means to said band means.

3. A method, as claimed in claim 2, wherein:
   said step of occupying a predetermined location includes coating said band means to promote the attachment of said marking means.

4. A method, as claimed in claim 1, wherein:
   said step of occupying a predetermined location includes forming a negative impression of the patient's teeth and transferring said marking means to said negative impression.

5. A method, as claimed in claim 4, wherein:
   said step of positioning said anchoring means includes attaching said anchoring means to said marking means in said negative impression.

6. A method, as claimed in claim 5, wherein:
   said step of positioning said anchoring means includes forming a positive cast of the patient's teeth and transferring said anchoring means to said positive cast.

7. A method, as claimed in claim 5, wherein:
   said step of positioning said anchoring means includes sealing at least one of said anchoring means and said marking means to prevent said anchoring means from adhering to said marking means when forming said positive cast.

8. A method, as claimed in claim 4, wherein:
   said step of forming a negative impression includes removing some of said negative impression material located adjacent to said marking means.

9. A method, as claimed in claim 4, wherein:
   said step of occupying a predetermined location includes providing marking means having an opening and locating said negative impression material in said opening.

10. A method for constructing a precise orthodontic appliance for a patient's teeth, comprising:
    defining a predetermined location relative to the current orientation of a patient's teeth that exist prior to the changed orientation that the precise orthodontic appliance is to achieve using marking means;
    positioning anchoring means in a positive cast using said marking means; and
    fabricating a precise orthodontic appliance for the patient's teeth using said anchoring means and said positive cast, wherein during said fabricating step the patient's teeth represented in the positive cast exist in said current orientation.

11. An apparatus for constructing a precise orthodontic appliance for a patient's teeth, comprising:
    first means provided in a negative impression of the patient's teeth for occupying a predetermined point in space exterior the negative impression of the patient's teeth and interior a space defined by an appliance attached to the patient's teeth; and
    second means provided in a positive casting of the patient's teeth for defining but not occupying said predetermined point in space exterior the teeth, said second means being removably attached to said first means in the negative impression.

12. An apparatus for use in constructing a precise orthodontic appliance, comprising:
    a marking device for indicating in a negative impression the point in space interior to but not occupied, by an orthodontic appliance attached to the patient s teeth, which said marking device comprises:
    orientation means, separate from the orthodontic appliance, for indicating the location of the orthodontic appliance attached to the patient's teeth; and
    means for holding said orientation means in a negative impression of the patient's teeth.

13. An apparatus, as claimed in claim 12 wherein: said means for holding said orientation means in said negative impression of the teeth includes retention means.

14. An apparatus for use in constructing a precise orthodontic appliance, comprising:
    a marking device for indicating in a negative impression the corresponding location of an orthodontic appliance attached to the patient's teeth;
    wherein said marking means comprises orientation means for indicating the location of the orthodontic appliance attached to the patient's teeth and retention means for holding said orientation means in a negative impression;
    wherein said orientation means comprises a vertical post for indicating the location of the orthodontic appliance attached to the patient's teeth.

15. An apparatus for use in constructing a precise orthodontic appliance, comprising:
    a marking device for indicating in a negative impression the corresponding location of an orthodontic appliance attached to the patient's teeth;

wherein said marking means comprises orientation means for indicating the location of the orthodontic appliance attached to the patient's teeth and retention means for holding said orientation means in a negative impression;

wherein said orientation means comprises two vertically disposed substantially parallel parts for indicating the location of the orthodontic appliance attached to the patient's teeth.

16. An apparatus for use in constructing a precise orthodontic appliance, comprising:

a marking device for indicating in a negative impression the corresponding location of an orthodontic appliance attached to the patient's teeth;

wherein said marking means comprises orientation means for indicating the location of the orthodontic appliance attached to the patient's teeth and retention means for holding said orientation means in a negative impression;

wherein said retention mean comprises a trapezoidal construction having an opening.

17. An apparatus for use in constructing a precise orthodontic appliance, comprising:

a marking device for indicating in a negative impression the corresponding location of an orthodontic appliance attached to the patient's teeth;

wherein said marking means comprises orientation means for indicating the location of the orthodontic appliance attached to the patient's teeth and retention means for holding said orientation means in a negative impression;

wherein said orientation means is angularly disposed relative to said retention means.

18. An apparatus for use in constructing a precise orthodontic appliance, wherein a first orthodontic appliance is attached to the patient's teeth and includes a first portion and remaining portions, which are other than the first portion, comprising:

anchoring means for simulating in a positive cast the first portion of the first orthodontic appliance attached to the patient's teeth; and holding means for joining said anchoring means to a positive cast wherein said holding means does not simulate the remaining portions of the first orthodontic appliance attached to the patient's teeth.

19. An apparatus, as claimed in claim 18, in which said anchoring means comprises:

a vertically disposed tube adapted to mate with a post of the orthodontic appliance.

20. An apparatus, as claimed in claim 18, in which said anchoring means comprises:

two vertically disposed, spaced parallel tubes.

21. An apparatus, as claimed in claim 18, in which said holding means comprises:

two retention tabs connection to and extending outwardly from said anchoring means, wherein said retention tabs are adapted to be held by the position cast.

22. An apparatus for constructing a precise orthodontic appliance for a patient's teeth, comprising:

first means provided in a negative impression of the patient's teeth for marking a predetermined location relative to the current orientation of a patient's teeth existing prior to the changed orientation that the precise orthodontic appliance is to achieve; and second means provided in a positive cast of patient's teeth for duplicating said predetermined location, said second means being removably attached to said first means using a negative impression.

* * * * *